(12) United States Patent
Nemovicher et al.

(10) Patent No.: US 10,568,662 B2
(45) Date of Patent: Feb. 25, 2020

(54) ORTHOPEDIC CLAMPING DEVICES

(71) Applicant: The Orthopaedic Implant Company, Reno, NV (US)

(72) Inventors: Itai Nemovicher, Reno, NV (US); Todd Martens, Denver, CO (US); Michael W. Mullaney, Naples, FL (US)

(73) Assignee: The Orthopaedic Implant Company, Reno, NV (US)

( * ) Notice: Subject to any disclaimer, the term of this patent is extended or adjusted under 35 U.S.C. 154(b) by 0 days.

(21) Appl. No.: 16/006,159

(22) Filed: Jun. 12, 2018

(65) Prior Publication Data
US 2019/0110814 A1    Apr. 18, 2019

Related U.S. Application Data

(60) Provisional application No. 62/571,571, filed on Oct. 12, 2017.

(51) Int. Cl.
  *A61B 17/64*   (2006.01)
  *A61B 90/57*   (2016.01)
  *A61B 17/00*   (2006.01)

(52) U.S. Cl.
  CPC ........ *A61B 17/645* (2013.01); *A61B 17/6466* (2013.01); *A61B 90/57* (2016.02); *A61B 2017/00477* (2013.01)

(58) Field of Classification Search
  CPC .......................................... A61B 17/645–6483
  See application file for complete search history.

(56) References Cited

U.S. PATENT DOCUMENTS

| 5,752,954 | A | * | 5/1998 | Mata | A61B 17/645 |
| | | | | | 606/59 |
| 5,976,133 | A | * | 11/1999 | Kraus | A61B 17/171 |
| | | | | | 606/54 |
| 8,523,858 | B2 | | 9/2013 | Lessig et al. | |

(Continued)

FOREIGN PATENT DOCUMENTS

| MX | 2012008576 | 1/2014 |
| MX | 2012008577 | 1/2014 |

OTHER PUBLICATIONS

Written Opinion and International Search Report issued in PCT/US2018/054797 filed Oct. 8, 2018, dated Mar. 19, 2019.

*Primary Examiner* — Nicholas J Plionis
(74) *Attorney, Agent, or Firm* — Heslin Rothenberg Farley & Mesiti P.C.; Kristian E. Ziegler; John W. Boger

(57) ABSTRACT

An orthopedic clamp for affixing at least two fixation members relative to each other is disclosed. The clamp includes a first clamp comprising first outer and inner jaws that define first clamping surfaces that form a first recess, and a second clamp comprising second outer and inner jaws that define second clamping surfaces that form a second recess. The clamps also include a post extending from the second outer jaw and through the second inner jaw, the first inner jaw and the first outer jaw. The post defines a clamping axis, and the second recess defines an axis that intersects the clamping axis. The clamp further includes a clamping nut threadably coupled to the post configured to exert a clamping force to the first and second clamps to fix at least one of a first fixation member within the first recess and a second fixation member within the second recess.

26 Claims, 14 Drawing Sheets

(56) References Cited

U.S. PATENT DOCUMENTS

| | | | |
|---|---|---|---|
| 8,734,446 B2* | 5/2014 | Miller | A61B 17/6466 606/277 |
| 9,050,135 B2* | 6/2015 | Dominik | A61B 17/6466 |
| 9,848,912 B1* | 12/2017 | Endara | A61B 17/645 |
| 9,943,337 B2* | 4/2018 | Muniz | A61B 17/6466 |
| 2006/0039750 A1* | 2/2006 | Thomke | A61B 17/645 403/385 |
| 2007/0198012 A1* | 8/2007 | Thomke | A61B 17/60 606/54 |
| 2007/0293860 A1* | 12/2007 | Oesch | A61B 17/645 606/60 |
| 2008/0247818 A1* | 10/2008 | Oesch | A61B 17/645 403/389 |
| 2010/0298827 A1* | 11/2010 | Cremer | A61B 17/6466 606/54 |
| 2011/0066151 A1* | 3/2011 | Murner | A61B 17/6466 606/54 |
| 2012/0004659 A1* | 1/2012 | Miller | A61B 17/6466 606/54 |
| 2012/0095462 A1* | 4/2012 | Miller | A61B 17/6466 606/59 |
| 2012/0296335 A1 | 11/2012 | Mullaney | |
| 2015/0119886 A1* | 4/2015 | Milella, Jr. | A61B 17/6466 606/59 |
| 2017/0281236 A1 | 10/2017 | Mussolin | |
| 2019/0029726 A1* | 1/2019 | Cremer | F16B 7/0493 |

\* cited by examiner

ORTHOPEDIC CLAMPING DEVICES

CROSS-REFERENCE TO RELATED APPLICATION

This present application perfects and claims the benefit of U.S. Provisional Patent Application No. 62/571,571, filed on Mar. 9, 2018, entitled Orthopedic Clamping Devices, the contents of which is hereby expressly incorporated herein by reference in its entirety.

FIELD OF THE INVENTION

The present disclosure is generally directed to clamps. More particularly, the present disclosure is directed to clamping devices of external fixation systems for stabilizing tissue, such as bone fragments.

BACKGROUND OF THE INVENTION

External fixation systems use pins, wires, rods or other fixation elements to stabilize and/or manipulate tissue segments, such as bone segments. These fixation elements are typically held in space relative to each other by a fixation frame. The frame is commonly made up of rings, struts, bars or other structural members. The simplest frame is usually made up of bars (sometimes referred to as rods). To hold the bars to each other and to the fixation elements, an orthopedic clamping device with two or more clamps is typically utilized. Clamps may also be employed to hold bars to rings, pins to rings, struts to rings, and other configurations.

A user typically constructs an external fixation system by placing fixation elements into tissue segments (e.g., bone segments) and assembling a frame into an approximate shape. One or more clamps is typically loosely coupled to the frame components and the fixation elements. The tissue segments are then manually adjusted into a desired or corrected anatomic arrangement or position. The frame is then locked into place by tightening the one or more clamps to fix the tissue segments in the desired or corrected anatomic arrangement.

Some orthopedic clamps are configured to create a frame with the fixation members (e.g., bars, pins, etc.) being snapped into the clamp. The clamps are constructed of two jaws, each with opposing channels the relative shape of half of the fixation member they are clamping (such as a bar or pin). The jaws are offset from the clamping axis (i.e., the axis or direction of the clamping or compression force applied to the clamps) and initially engage at a backside across the clamping axis such that the jaws pivot toward or away from each other along the clamping axis. The jaws are biased towards each other along the clamping axis by spring elements. When the bar or pin is snapped into the jaw, the spring elements hold the jaws against the fixation member. This makes assembly easy, but the spring sand the jaws often allow for the fixation member to pop out when the assembly is being adjusted into the appropriate or desired position. Some other orthopedic clamps include two jaws that slide relative to each other perpendicular to the clamping axis. The direction of opening of the jaws of such clamps is such that force applied by the fixation member against the jaw does not cause the jaw to open.

A drawback of current orthopedic clamps is that their configuration tends to allow the bars or rods to decouple from the jaws of the clamp when the assembly and tissue segments are adjusted. Another drawback of current orthopedic clamps is that because they rely on clamping surfaces or recesses of the jaws that are offset from the clamping axis, the backside of the clamps must abut to pivot the jaws closed. As clamping pressure is applied, the clamping force is thereby split or shared between the backside of the clamps and the fixation member between the jaws.

As a result, orthopedic clamps that direct all, or at least the majority, of the clamping pressure to the clamping surfaces of the jaws thereof, and thereby to a fixation member (e.g., a rod or pin) therebetween, is desirable. Further, orthopedic clamps that tend to prevent fixation members from disconnecting from the clamp when the assembly and/or tissue segments are adjusted is also desirable.

SUMMARY OF THE INVENTION

In one aspect, the present disclosure provides a clamp for affixing at least two fixation members relative to each other. The clamp includes a first clamp comprising a first outer jaw and a first inner jaw that define first clamping surfaces that form a first recess that is open to a front side of the first clamp. The clamp also includes a second clamp comprising a second outer jaw and a second inner jaw that define second clamping surfaces that form a second recess that is open to a front side of the second clamp. The clamp further includes a post fixed to the second outer jaw and extending through an internal aperture and past the first outer jaw, the post defining a clamping axis. The clamp also includes a clamping nut threadably coupled to the post configured to exert a clamping force to the first and second clamps to fix a first fixation member positioned within the first recess and a second fixation member positioned within the second recess.

In another aspect, the present disclosure provides a clamp for affixing at least two fixation members relative to each other. The clamp includes a first clamp comprising a first outer jaw and a first inner jaw that define first clamping surfaces that form a first recess that is open to a front side of the first clamp. The clamp also includes a second clamp comprising a second outer jaw and a second inner jaw that define second clamping surfaces that form a second recess that is open to a front side of the second clamp. The clamp further includes a post fixed to the second outer jaw and extending through an internal aperture and past the first outer jaw, the post defining a clamping axis. The clamp also includes a clamping nut threadably coupled to the post configured to exert a clamping force to the first and second clamps to fix a first fixation member positioned within the first recess and a second fixation member positioned within the second recess. The axis of the second recess and/or the second fixation member intersects the clamping axis.

In another aspect, the present disclosure provides a clamp for affixing at least two fixation members relative to each other. The clamp includes a first clamp comprising a first outer jaw and a first inner jaw that define first clamping surfaces that form a first recess that is open to a front side of the first clamp. The clamp also includes a second clamp comprising a second outer jaw and a second inner jaw that define second clamping surfaces that form a second recess that is open to a front side of the second clamp. The clamp further includes a post fixed to the second outer jaw and extending through an internal aperture and past the first outer jaw, the post defining a clamping axis. The clamp also includes a clamping nut threadably coupled to the post configured to exert a clamping force to the first and second clamps to fix a first fixation member positioned within the first recess and a second fixation member positioned within the second recess. The second clamp is configured such that the clamping force is applied to the second fixation member and not directly between the second outer jaw and a second inner jaw.

In another aspect, the present disclosure provides a clamp for affixing at least two fixation members relative to each other. The clamp includes a first clamp comprising a first outer jaw and a first inner jaw that define first clamping surfaces that form a first recess that is open to a front side of the first clamp. The clamp also includes a second clamp comprising a second outer jaw and a second inner jaw that define second clamping surfaces that form a second recess that is open to a front side of the second clamp. The clamp further includes a post fixed to the second outer jaw and extending through an internal aperture and past the first outer jaw, the post defining a clamping axis. The clamp also includes a clamping nut threadably coupled to the post configured to exert a clamping force to the first and second clamps to fix a first fixation member positioned within the first recess and a second fixation member positioned within the second recess. The clamp further includes a resilient member positioned between the first outer jaw and the clamping nut along the clamping axis that exerts an adjustment clamping force to the first and second clamps to maintain engagement of the first fixation member within the first recess and the second fixation member within the second recess during manipulation of the first and second fixation members prior to the exertion of the fixation clamping force.

In another aspect, the present disclosure provides a clamp for affixing at least two fixation members relative to each other. The clamp comprises a first clamp comprising a first outer jaw and a first inner jaw that define first clamping surfaces that form a first recess that is open to a front side of the first clamp, and a second clamp comprising a second outer jaw and a second inner jaw that define second clamping surfaces that form a second recess that is open to a front side of the second clamp. The clamp also comprises a post extending from the second outer jaw and extending through the second inner jaw, the first inner jaw and the first outer jaw, the post defining a clamping axis. The clamp further comprises a clamping nut threadably coupled to the post configured to exert a clamping force to the first and second clamps to fix at least one of a first fixation member positioned within the first recess and a second fixation member positioned within the second recess.

In some embodiments, the second recess of the second clamp defines an axis, and wherein the axis of the second recess intersects the clamping axis. In some such embodiments, the second fixation member defines an axis, and the axis of the second fixation member intersects the clamping axis when the second fixation member is positioned within the second recess of the second clamp. In some other such embodiments, the second fixation member defines an axis, and the axis of the second fixation member intersects the clamping axis when the second fixation member is positioned within the second recess of the second clamp. In some other such embodiments, the axis of the second recess and the clamping axis are perpendicular. In some other such embodiments, the second clamping surfaces of the second outer and inner jaws define a third recess that is positioned between the second recess and the front side of the second clamp. In some such embodiments, the third recess is open at the front side of the second clamp and the second recess is open to the third recess.

In some embodiments, the second clamp is configured such that the clamping force is applied to the second fixation member positioned within the second recess and not directly between the second outer jaw and the second inner jaw. In some such embodiments, the second clamp is configured such that the clamping force is not applied to backside surfaces of the of the second outer jaw and the second inner jaw at a back side of the second clamp that is on an opposing side of the clamping axis as the front side of the second clamp when the clamping force is applied to the second fixation member positioned within the second recess. In some such embodiments, the second clamp is configured such that a gap is formed between the backside surfaces of the second outer jaw and the second inner jaw when the clamping force is applied to the second fixation member positioned within the second recess.

In some embodiments, the first recess of the first clamp defines an axis, and the axis of the first recess is perpendicular to the clamping axis. In some embodiments, the clamp further comprises a resilient member that exerts an adjustment clamping force to the first and second clamps to maintain engagement of at least one of the first fixation member within the first recess and the second fixation member within the second recess during manipulation thereof prior to exertion of the fixation clamping force via the clamping nut. In some such embodiments, the resilient member is positioned between the first outer jaw and the clamping nut along the clamping axis.

In some embodiments, the first inner jaw of the first clamp and the second inner jaw of the second clamp are in abutment along engagement surfaces thereof, and the engagement surfaces of the first and second inner jaws are configured such that the relative rotational arrangement of the first and second clamps about the camping axis is fixed when the clamping force is applied.

In another aspect, the present disclosure provides a clamp for affixing at least two fixation members relative to each other. The clamp comprises a first clamp comprising a first outer jaw and a first inner jaw that define first clamping surfaces that form a first recess that is open to a front side of the first clamp, and a second clamp comprising a second outer jaw and a second inner jaw that define second clamping surfaces that form a second recess that is open to a front side of the second clamp. The second recess defines an axis. The clamp also comprises a post extending from the second outer jaw and past the first outer jaw that defines a clamping axis that intersects the axis of the second recess. The clamp further comprises a clamping nut threadably coupled to the post configured to exert a clamping force to the first and second clamps to fix at least one of a first fixation member positioned within the first recess and a second fixation member positioned within the second recess.

In some embodiments, the axis of the second recess and the clamping axis are perpendicular. In some embodiments, the second clamp is configured such that the clamping force is applied to the second fixation member positioned within the second recess and not directly between the second outer jaw and the second inner jaw. In some such embodiments, the second clamp is configured such that the clamping force is not applied to backside surfaces of the of the second outer jaw and the second inner jaw at a back side of the second clamp that is on an opposing side of the clamping axis as the front side of the second clamp when the clamping force is applied to the second fixation member positioned within the second recess. In some such embodiments, the second clamp is configured such that a gap is formed between the backside surfaces of the second outer jaw and the second inner jaw when the clamping force is applied to the second fixation member positioned within the second recess.

In some embodiments, the first inner jaw of the first clamp and the second inner jaw of the second clamp are in abutment along engagement surfaces thereof, and the engagement surfaces of the first and second inner jaws are configured such that the relative rotational arrangement of the first and second clamps about the camping axis is fixed when the clamping force is applied. In some embodiments, the clamp further comprises a resilient member that exerts an adjustment clamping force to the first and second clamps to maintain engagement of at least one of the first fixation member within the first recess and the second fixation member within the second recess during manipulation thereof prior to exertion of the fixation clamping force via the clamping nut.

These and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the orthopedic clamping devices described herein, illustrative embodiments are provided. These illustrative embodiments are in no way limiting in terms of the precise configuration, arrangement and operation of the disclosed orthopedic clamping devices, and other similar embodiments are envisioned.

DETAILED DESCRIPTION

Figure 2:
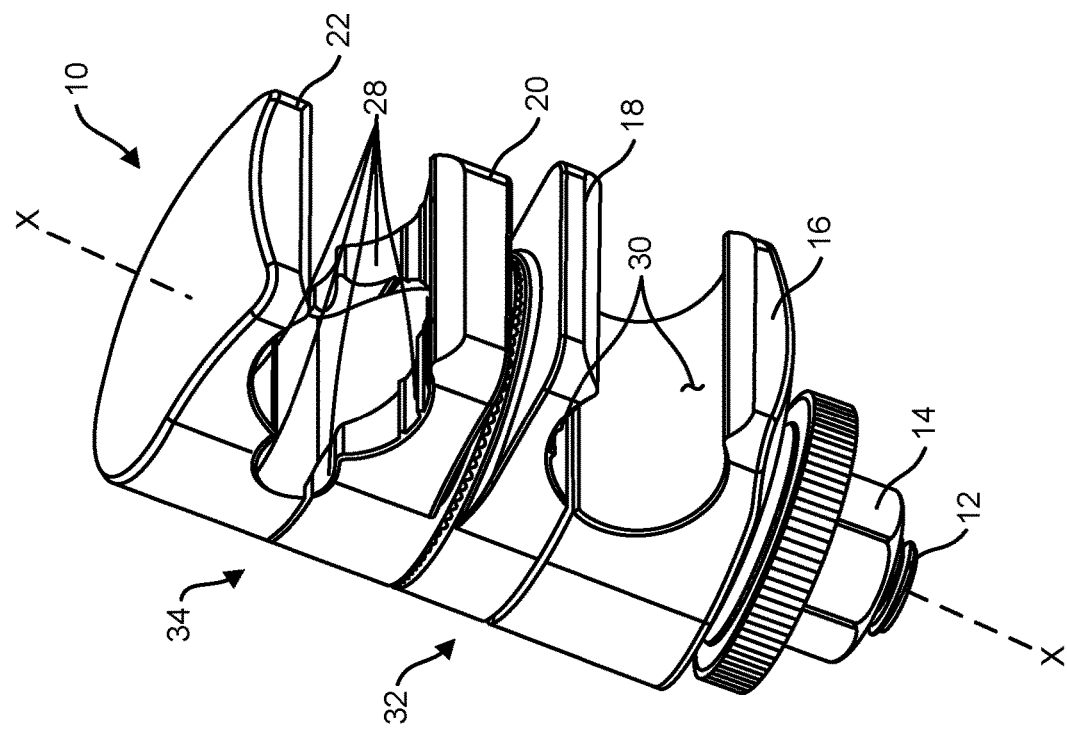
FIG. 2 is a front perspective view of the orthopedic clamping device of FIG. 1.
Figure 1:
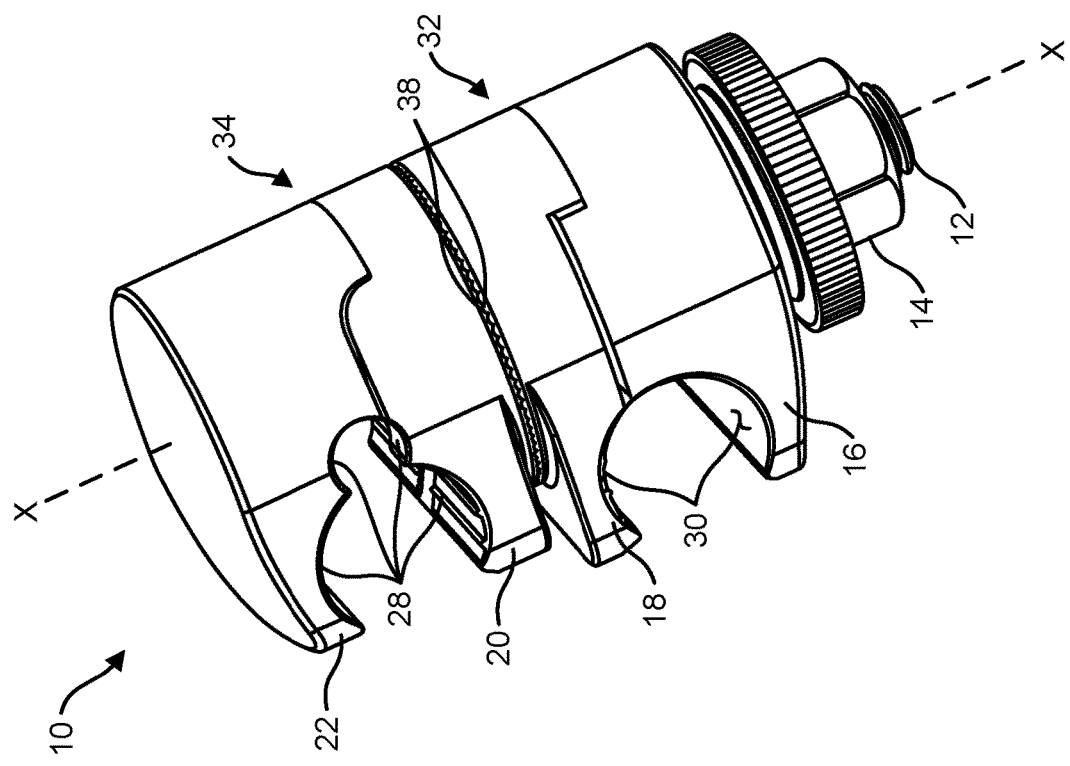
FIG. 1 is a rear perspective view of an exemplary orthopedic clamping device according to the present disclosure.
Figure 4:
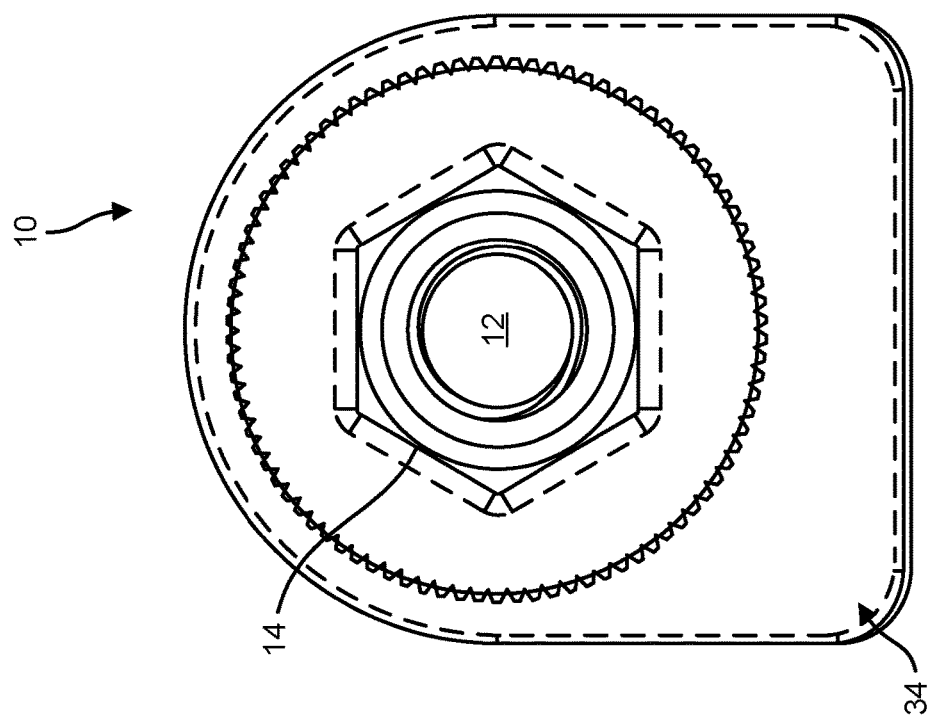
FIG. 4 is a bottom view of the orthopedic clamping device of FIG. 1.
Figure 3:
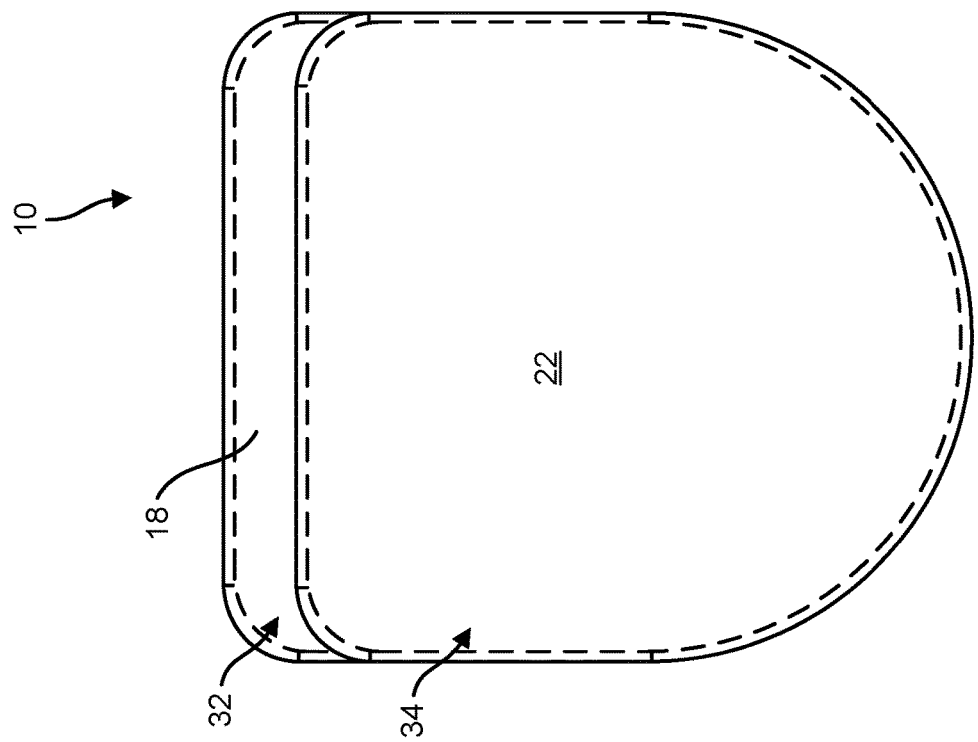
FIG. 3 is a top view of the orthopedic clamping device of FIG. 1.
Figure 5:
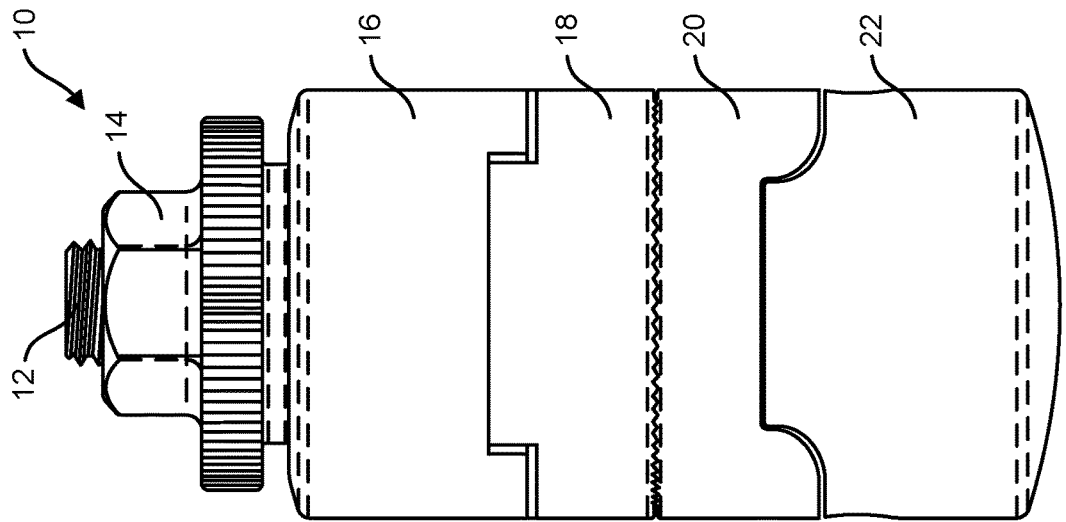
FIG. 5 is a side view of the orthopedic clamping device of FIG. 1.
Figure 6:
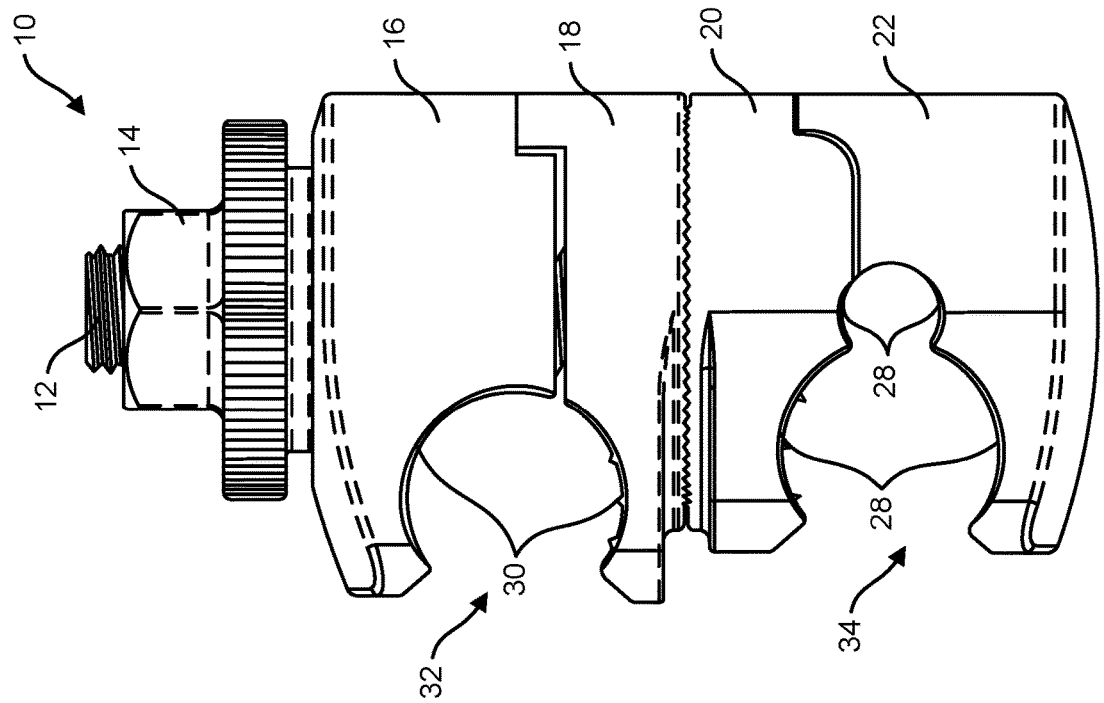
FIG. 6 is a back view of the orthopedic clamping device of FIG. 1.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

The present disclosure provides orthopedic clamping devices or systems that direct all, or at least the majority, of the fixation clamping pressure to the clamping or engagement surfaces of the jaws thereof, and thereby to a fixation member (e.g., a rod or pin) therebetween. Further, the present disclosure provides orthopedic clamping devices or systems that tend to prevent fixation member from disconnecting from the clamp when the assembly and tissue segments are adjusted prior to applying the fixation clamping pressure.

An exemplary orthopedic clamping device or system 10 according to the present disclosure is shown in FIGS. 1-12. As shown in FIGS. 1-12, the clamping device 10 includes a first clamp 32 and a second clamp 34. The clamping device 10 may include just one of the first or second clamps 20, 22, or include three or more clamps. As shown in FIGS. 1-12, both the first clamp 32 and the second clamp 34 may be configured to removably couple with at least one fixation member, such as a cylindrical bar, rod, pin, etc. In some embodiments, as also shown in FIGS. 1-12, the first clamp 32 may be configured to removably couple one fixation member (such as a cylindrical bar, rod or pin), and the second clamp 34 may be configured to removably couple two differing fixation members (such as a cylindrical bar or rod and a cylindrical pin of a small diameter as compared to the bar or rod). However, in some embodiments the first clamp 32 may be configured to removably couple with more than one fixation member, and the second clamp 34 may be configured to removably couple with only one fixation member.

As shown in FIGS. 1-12, the first clamp 32 may include an outer jaw 16 and an inner jaw 18. A front side portion of both the inner and outer jaws 16, 18 may include a cylindrical recess or cavity formed by clamping faces or surfaces 30 (e.g., positioned between the inner and outer jaws 16, 18). The recessed clamping faces 30 may at least generally face each other and may be configured to engage a cylindrical fixation member, such as a rod or bar. For example, the clamping faces 30 may be arcuate such that they cooperate to form a cylindrical recess or cavity extending across the first clamp 32 that mimics or corresponds to a cylindrical fixation member. The cylindrical recess of the first clamp 32 may be open at the front side of the first clamp 32 to allow a fixation member (e.g., a bar or rod) to be slipped or translated laterally between the inner and outer jaws 16, 18 and into the recess. The recessed clamping faces 30 of the inner and outer jaws 16, 18 of the first clamp 32 may thereby be configured to clamp onto and secure to a fixation member, such as a bar or rod of an orthopedic fixation system, when a clamping force is exerted to the inner and outer jaws 16, 18.

The inner and outer jaws 16, 18 of the first clamp 32 may abut at a backside thereof that opposes the recessed clamping faces 30, as shown in FIGS. 1-12. The clamping faces 30 and the backside of the inner and outer jaws 16, 18 may thereby be on opposing sides of the clamping axis X-X, as described further below. The backside of the inner and outer jaws 16, 18 may initially abut when a clamping force is applied to the first clamp 32 so that the inner and outer jaws 16, 18 pivot and the recessed clamping faces 30 move closer to each other and/or apply a compressive force to a fixation member positioned therebetween (within the cylindrical recess formed thereby). As shown in FIGS. 2, 5, 6 and 9-12, the backside of the inner and outer jaws 16, 18 of the first clamp 32 may also be shaped and otherwise configured to prevent rotation therebetween about the clamping axis X-X. For example, the backside of the inner and outer jaws 16, 18 of the first clamp 32 may be keyed together to prevent rotation therebetween about the clamping axis X-X. In some embodiments, the backside of the inner and outer jaws 16, 18 of the first clamp 32 may also be shaped and otherwise configured to prevent translational movement therebetween.

Similar to the first clamp 32, the second clamp 34 may include an outer jaw 22 and an inner jaw 20, as shown in FIGS. 1-12. A front side portion of the second clamp 34 may include two adjacent cylindrical recesses or cavities formed by clamping faces or surfaces 28 (e.g., positioned between the inner and outer jaws 16, 18). The recessed clamping faces 28 of the inner and outer jaws 20, 22 may at least generally face toward each other and be configured to engage two differing fixation members (e.g., members of differing exterior diameters) (either independently or simultaneously), such as a rod/bar and a pin, two bars, or two pins. For example, the clamping faces 28 may each include two outer arcuate surface portions that cooperate to form an outer cylindrical recess of a first diameter for a first fixation member (e.g., a rod/bar) extending across the second clamp 34 that is open at the front of the second clamp (to allow the first fixation member to be slipped or translated laterally between the inner and outer jaws 20, 22 and into the recess), and an inner cylindrical recess of a second diameter that is smaller than the first diameter for a second fixation member (e.g., a pin) extending across the second clamp 34 that is positioned interior of the outer recess and is open thereto (to allow the second fixation member to be slipped or translated laterally from the outer recess and therein), as shown in FIGS. 1-12. In some embodiments, the outer and inner cylindrical recesses may thereby be an outer cylindrical bar or rod recess or opening and an inner cylindrical pin recess, respectively, for example. However, in other embodiments the outer and inner cylindrical recesses of the second clamp 34 may not be bar and pin recesses, the diameter of the inner cylindrical recess may larger than the outer cylindrical recess, or the diameter of the inner and outer cylindrical recesses may be substantially the same. As another example, the second clamp 34 may form only one recess, such as the inner cylindrical recess.

The axis of the inner cylindrical recess or opening, such as the axis of a pin recess, formed by the inner and outer jaws 20, 22 of the second clamp 34 may be aligned with (i.e., intersect), and potentially oriented perpendicular to, the clamping axis X-X of the clamp 10. The clamping axis X-X of the clamp 10, as shown in FIGS. 1, 2, 8 and 9, may be the axis or direction of the clamping or compression force on the first and second clamps 32, 34 (e.g., the axis of a clamping post 12), as described further below. The recessed clamping faces 28 of the inner and outer jaws 20, 22 of the second clamp 34 may thereby be configured to fixedly clamp onto and secure a fixation member, such as a bar/rod and/or pin of an orthopedic fixation system, that is aligned with and oriented perpendicular to the clamping axis X-X of the clamp 10 (i.e., the axis of the threaded rod 12). The second clamp 34 may thereby direct all, or at least the majority of, the clamping forces applied thereto to the fixation member positioned within the inner recesses via the recessed clamping faces 28.

As explained further below, the backside of the inner and outer jaws 20, 22 of the second clamp 34 that oppose the recessed clamping faces 30 may initially be spaced from each other when the clamping faces 30 engage at least one fixation member (e.g., a bar/rod and/or a pin) and a clamping force is applied to the second clamp 34 so that the clamping force is fully or at least predominantly applied to the at least one fixation member, as explained further below. The clamping faces 28 and the backside of the inner and outer jaws 20, 22 may thereby be on opposing sides of the clamping axis X-X. As shown in FIGS. 2, 5, 6 and 9-12, the backside of the inner and outer jaws 20, 22 of the second clamp 34 may also be shaped and otherwise configured to prevent rotation therebetween about the clamping axis X-X. For example, the backside of the inner and outer jaws 20, 22 of the second clamp 34 may be keyed together to prevent rotation therebetween about the clamping axis X-X. In some embodiments, the backside of the inner and outer jaws 20, 22 of the second clamp 34 may also be shaped and otherwise configured to prevent translational movement between therebetween.

As shown in FIGS. 8-12, the outer jaw 22 of the second clamp 34 may include a stem portion 40 that extends into an internal aperture of the inner jaw 20 of the second clamp 34 and, potentially, the inner jaw 18 of the first clamp 32. The configuration (e.g., size and shape) of the stem portion 40 and the internal aperture of the inner jaw 20 may be configured to prevent relative rotation, or at least limit relative rotation, of the components about the clamping axis X-X. In some embodiments, the configuration of the stem portion 40 and the internal aperture of the inner jaw 20 may be configured to limit relative movement between the outer jaw 22 and inner jaw 20 when the clamping surfaces 28 engage a fixation member.

Figure 8:
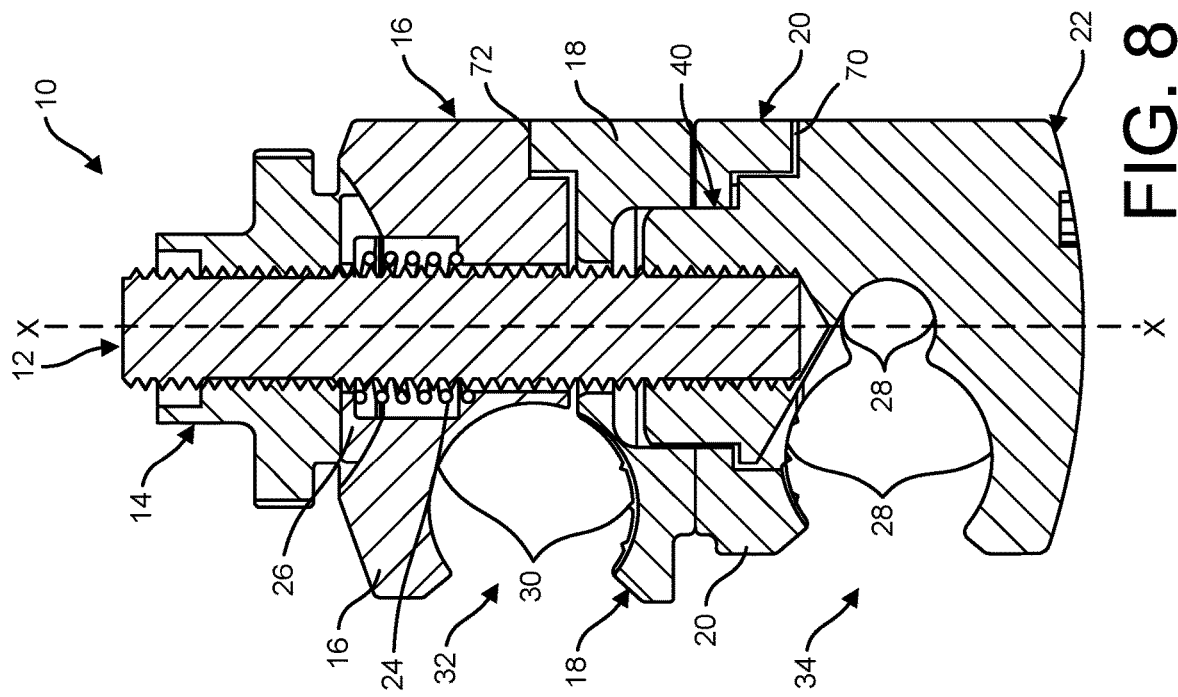
FIG. 8 a cross-sectional view of the orthopedic clamping device of FIG. 1 taken along line 8-8 as indicated in FIG. 7.
Figure 7:
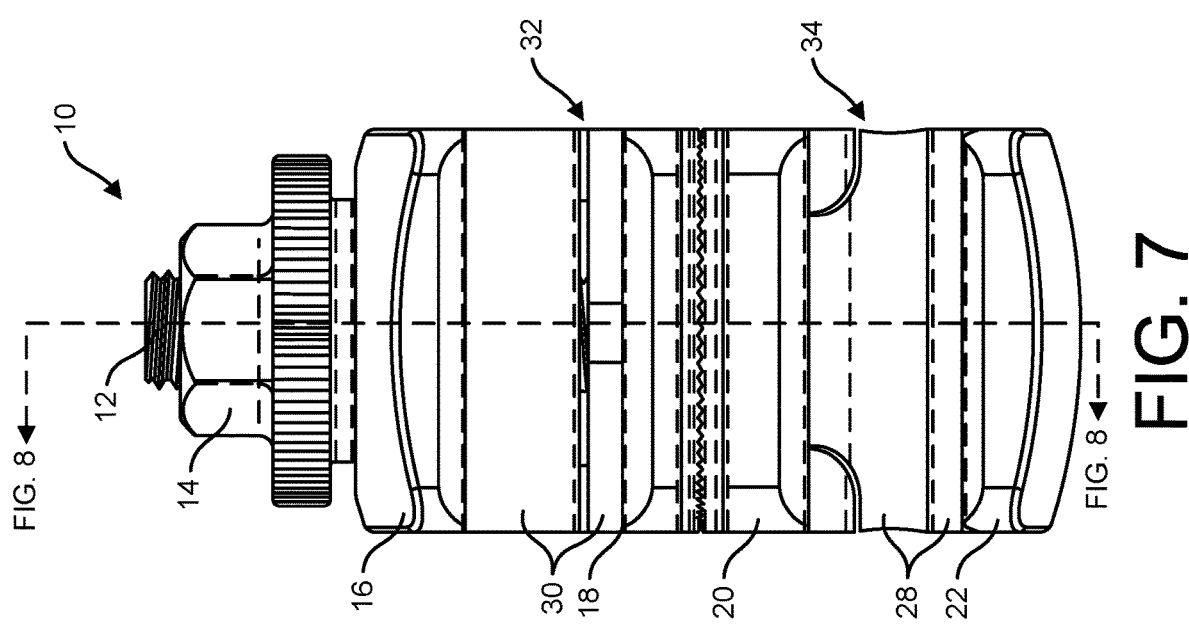
FIG. 7 is a front view of the orthopedic clamping device of FIG. 1.

The threaded post 12 may extend from or otherwise be coupled to the stem portion 40 of the outer jaw 22, as shown in FIG. 8. The outer jaw 22 is thereby able to form the recessed clamping surface 28 directly above the threaded post 12, as shown in FIGS. 8-12. The clamping surface 28 of the outer jaw 22 may thereby include an inner portion that is aligned with, and oriented perpendicular to, the clamping axis X-X. For example, the clamping surface 28 may define an inner cylindrical surface portion or recess (e.g., an arcuate surface defined by a radius and extended along an axis) that defines an axis that is aligned with (i.e., intersects) and is perpendicular to the clamping axis X-X, as shown in FIGS. 8-12. The inner cylindrical surface portion of the clamping surface 28 of the outer jaw 22 may thereby extend across the width of the outer jaw 22 and through the clamping axis X-X.

The recessed clamping surface 28 of the inner jaw 20 of the second clamp 34 may also define a corresponding inner cylindrical surface portion or recess (e.g., arcuate surface defined by a radius and extends along an axis) that defines an axis that is aligned with (i.e., intersects) and is perpendicular to the clamping axis X-X. Due to the stem portion 40 of the outer jaw 22 and the internal aperture of the inner jaw 20 that accommodates the stem portion 40, the inner cylindrical surface portion 28 cannot extend through the clamping axis X-X. As a result, the inner jaw 20 of the second clamp 34 may include two recessed clamp surface portions 28 positioned on either lateral side of the internal aperture of the inner jaw 20. The two recessed clamping surface portions 28 may be cylindrical surface portions or recesses that define an axis that is aligned with (i.e., intersects) and is perpendicular to the clamping axis X-X (and is aligned and parallel to the axis of the clamping surfaces 28 of the outer jaw 22), as shown in FIGS. 8-12. In this way, the recessed clamping surface 28 of the inner jaw 20 and the outer jaw 22 of the second clamp 34 may cooperate to form a cylindrical channel or recess with an axis that intersects (and is potentially perpendicular to) the clamping axis X-X (i.e., the axis of the clamping force). The recessed clamping surface 28 of the outer jaw 22 and the recessed clamping surfaces 28 of the inner jaw 20 (on opposing lateral sides of the clamping axis X-X) may thereby directly apply all, or at least substantially all, of the clamping or compressive force applied to the second clamp 34 onto a fixation member (e.g., a pin) positioned therebetween.

Figure 9:
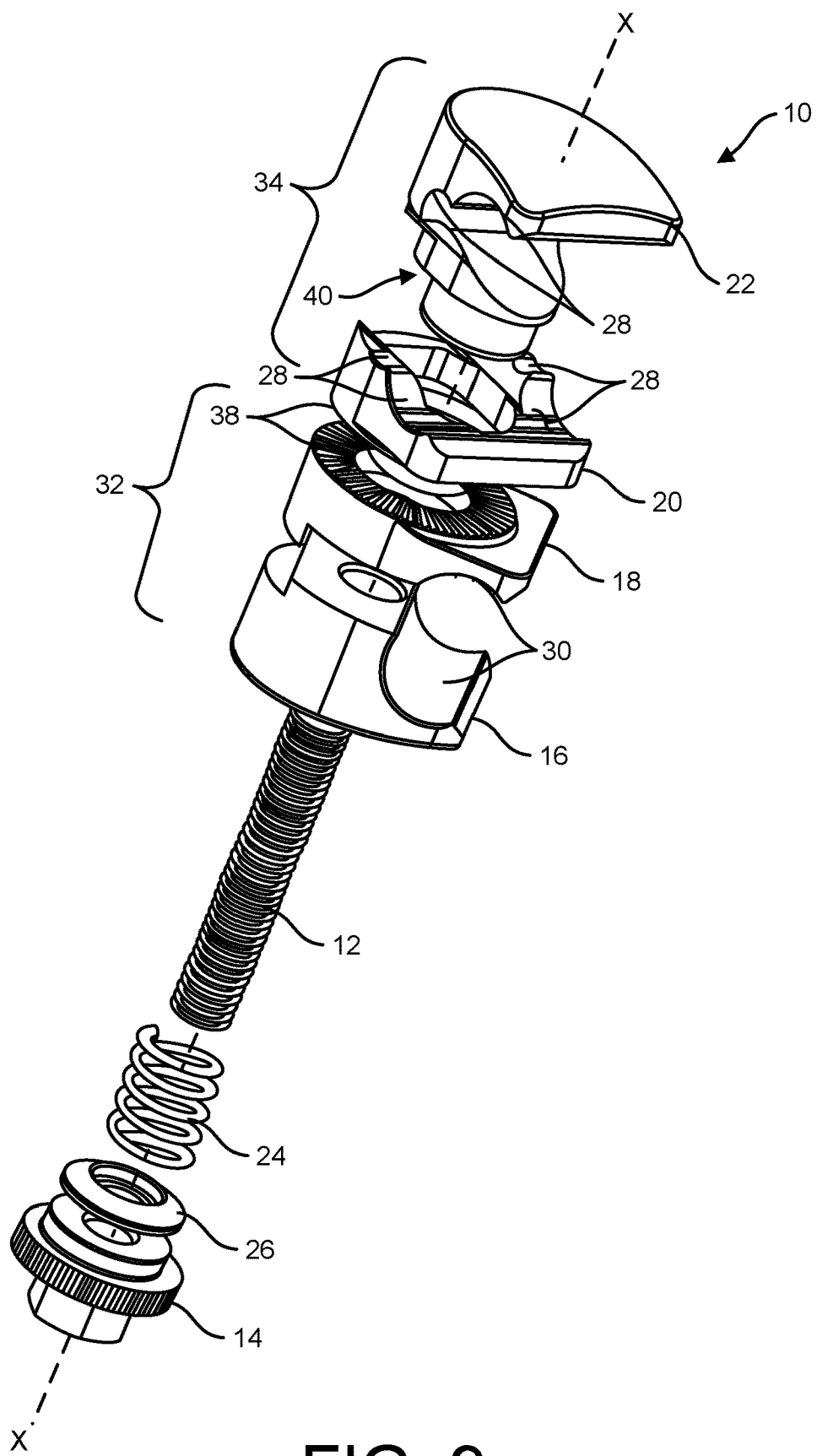
FIG. 9 is an elevational perspective exploded view of the orthopedic clamping device of FIG. 1 with the first and second clamps rotated with respect to each other.
Figure 10:
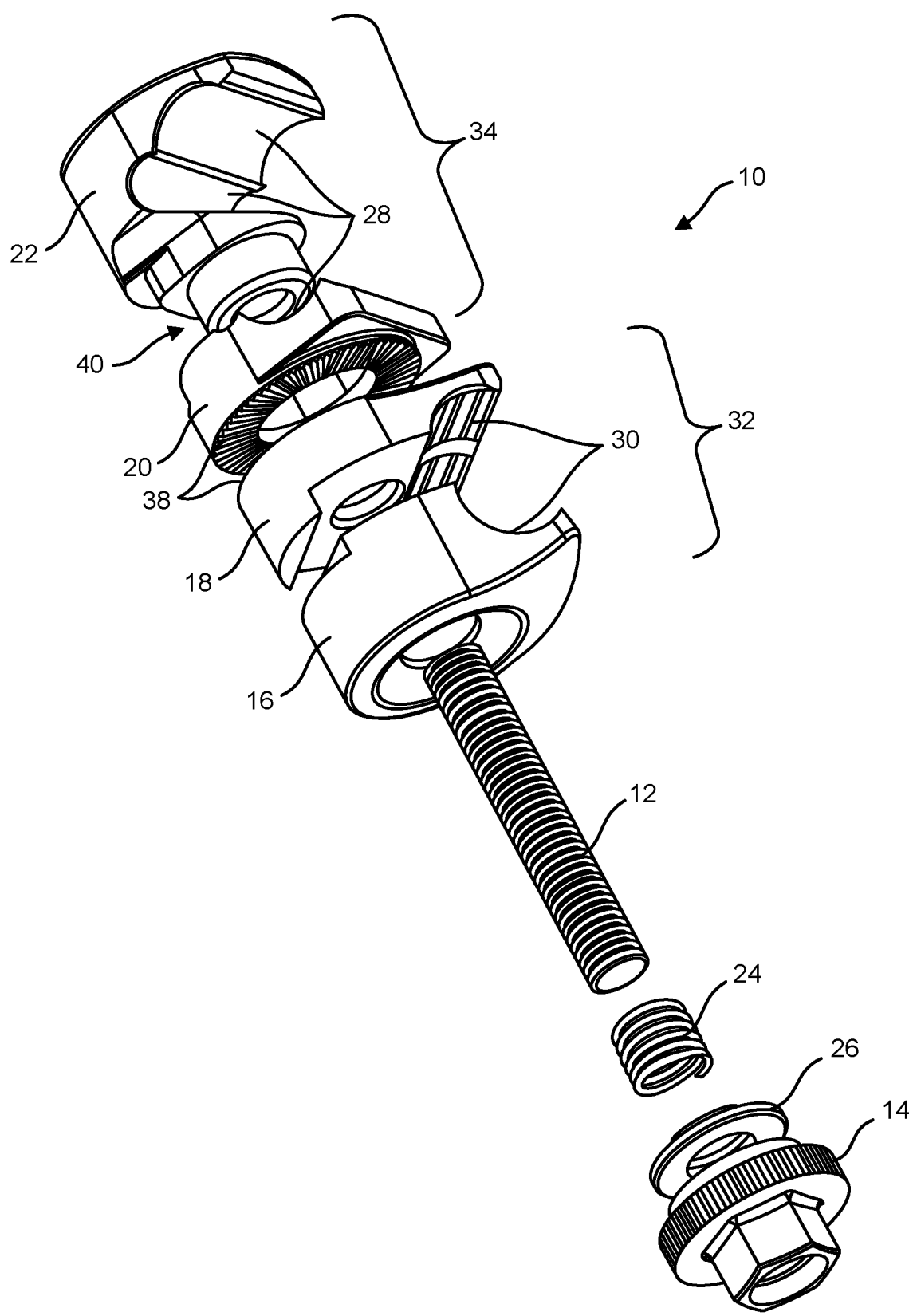
FIG. 10 is a bottom perspective exploded view of the orthopedic clamping device of FIG. 1 with the first and second clamps rotated with respect to each other.
Figure 11:
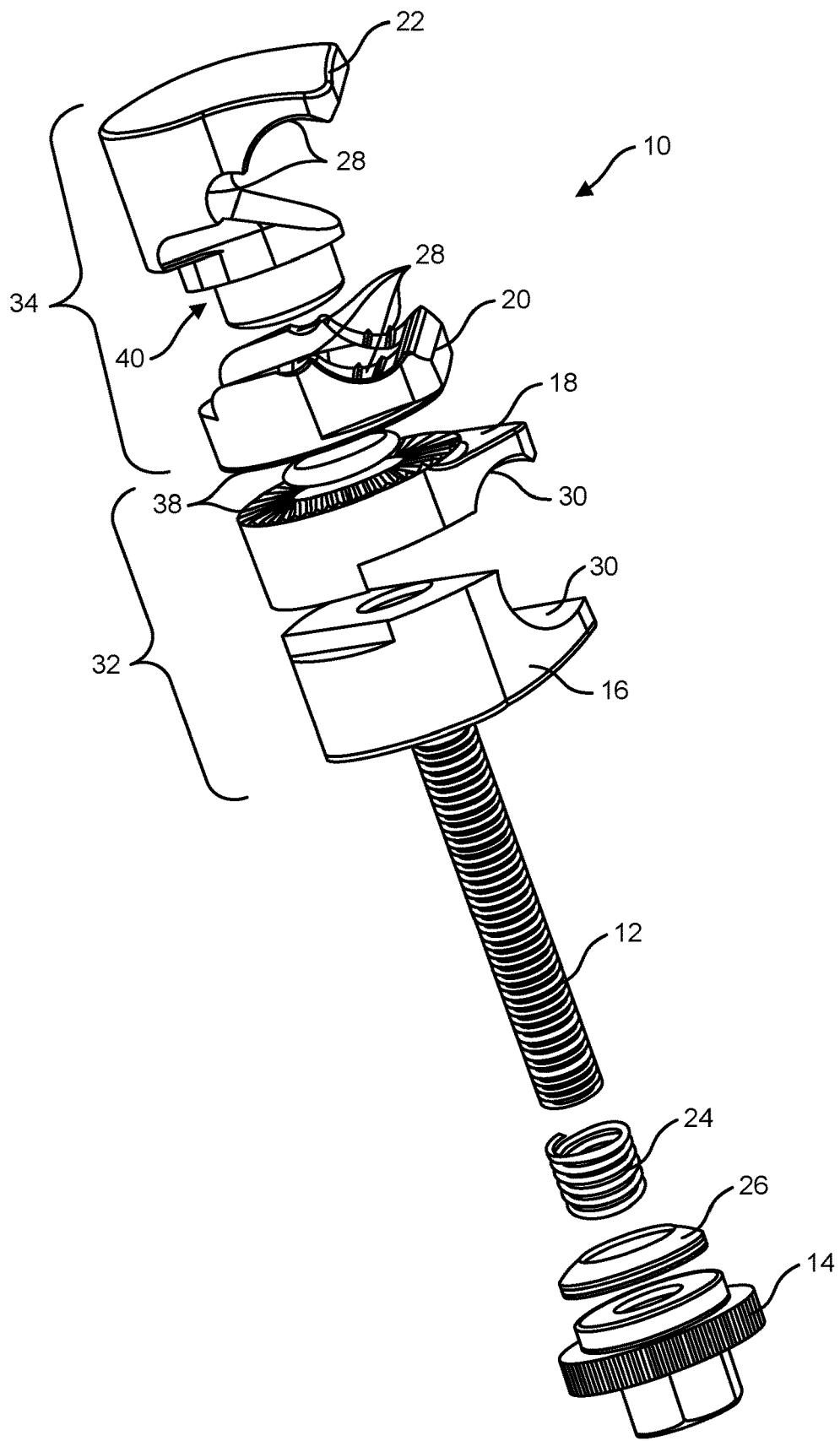
FIG. 11 is a perspective exploded view of the orthopedic clamping device of FIG. 1 with the first and second clamps rotated with respect to each other.
Figure 12:
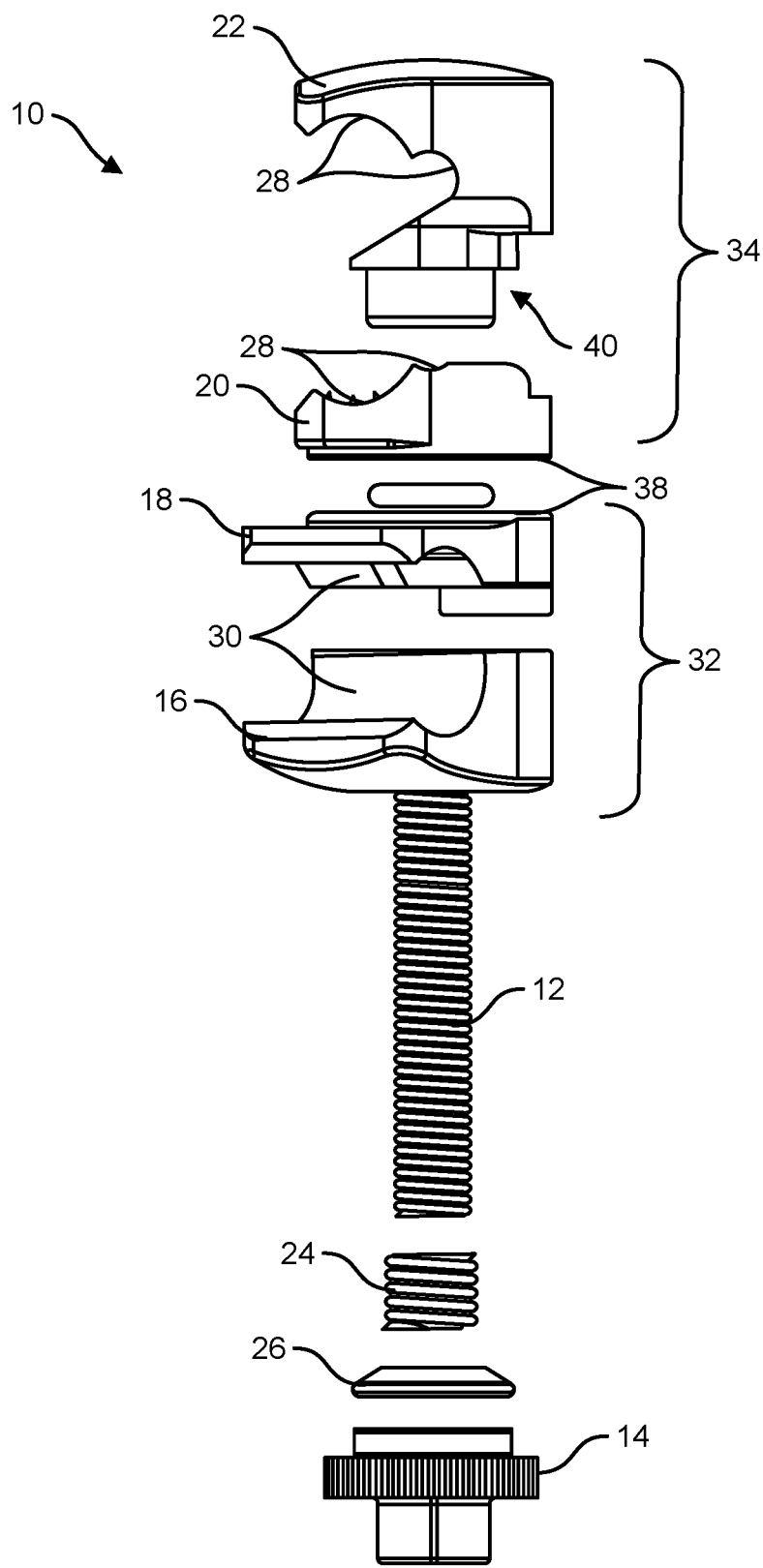
FIG. 12 is a side exploded view of the orthopedic clamping device of FIG. 1 with the first and second clamps rotated with respect to each other.
Figure 13:
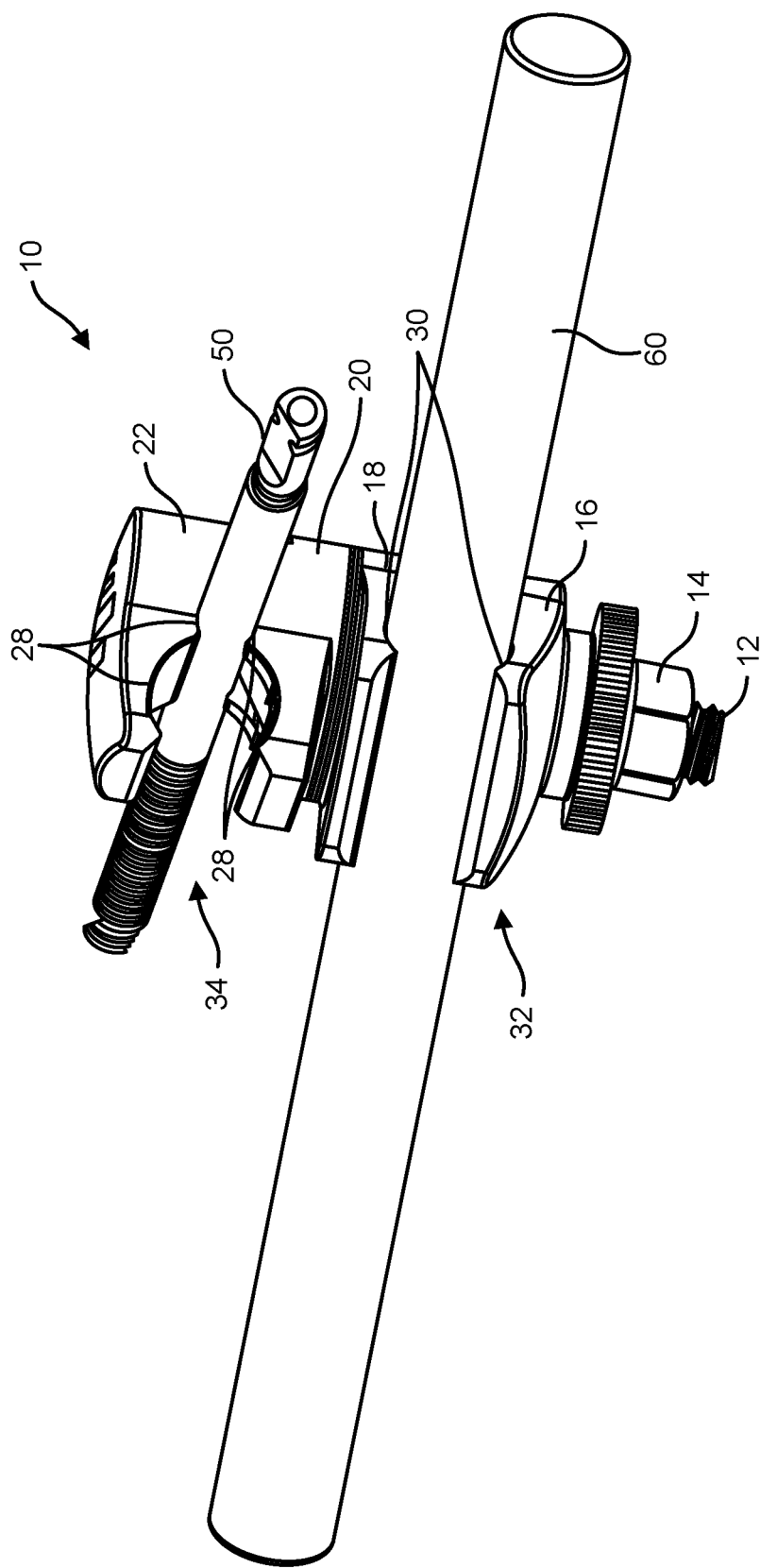
FIG. 13 is a perspective view of the orthopedic clamping device of FIG. 1 coupled to an exemplary orthopedic pin and an exemplary orthopedic rod or bar.
Figure 14:
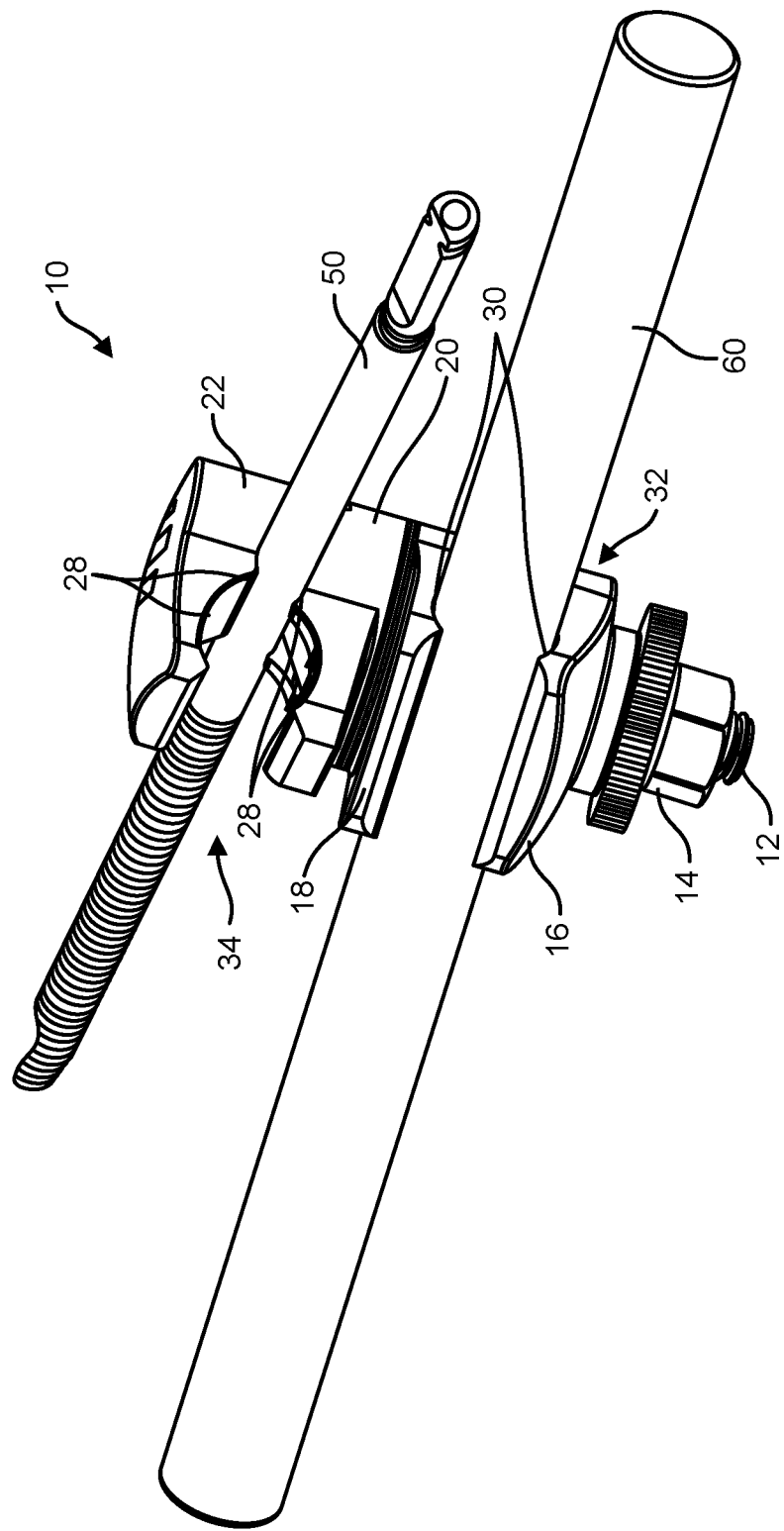
FIG. 14 is another perspective view of the orthopedic clamping device of FIG. 1 coupled to the exemplary pin and the exemplary rod.

As shown in FIGS. 1-12, the first clamp 32 and the second clamp 34 of the clamping device 10 may be rotatable with respect to each other about the clamping axis X-X of the clamp 10. The inner jaw 18 of the first clamp 32 and the inner jaw 20 of the second clamp 34 may be configured to securely abut against each other such that the movement (about all axes) therebetween is prevented when a clamping force is applied. For example, angulation and rotation of the inner jaws 18, 20 about the clamping axis X-X of the clamp 10 may be prevented by the configuration of the engagement surfaces 38 thereof, as shown in FIGS. 1 and 9-12. As shown in FIGS. 1-12, the inner jaws 18, 20 may include generally planar engagement surfaces 38 that include a surface texture or pattern to prevent relative movement therebetween. The engagement surfaces 38 may align the inner jaws 18, 20 in a preferred rotational arrangement about the clamping axis X-X, and maintain such rotational alignment and alignment along all three orthogonal axes. For example, the engagement surfaces 38 of the inner jaws 18, 20 may include circumferential radially extending ridges and grooves (a poker chip configuration), as shown in FIGS. 9-11. In some embodiments, the engagement surfaces 38 of the inner jaws 18, 20 may be configured such that that they are parallel to each other when engaged.

The clamp 10 may also include a tightening or clamping nut 14 rotatably coupled to an externally threaded post 12, as shown in FIGS. 1-12. At least a portion of the post 12 may be threaded, such as externally threaded. The threaded post 12 may extend from the outer jaw 22 of the second clamp 34 and past the outer jaw 16 of the first clamp 32. In some embodiments, the threaded post 12 may extend through an internal or central aperture in the inner jaw 18, outer jaws, and/or the inner jaw 20. It is noted that the apertures within the inner and outer jaws 18, 16 of the first clamp 32 and the inner jaw 20 of the first clamp 32 may be larger than the threaded post 12 (and or a stem portion 40 of the outer jaw 22) such that a gap or space is formed between the post 12 and the inner and outer jaws 18, 16 of the first clamp 32 and/or the inner jaw 20 of the first clamp 32, as shown in FIG. 8. Such gaps may allow some movement of the inner and outer jaws 18, 16 of the first clamp 32 and the inner jaw 20 of the first clamp 32 with respect to the post 12 when a clamping force is applied to the clamp 10, as described further below.

As shown in FIG. 8, the post 12 may extend into an internal or central aperture or cavity of the outer jaw 22 of the second clamp 34. The threaded post 12 may be coupled or fixed to the outer jaw 22 of the second clamp 34 such that movement (including rotation) of the threaded post 12 with respect to the outer jaw 22 is prevented. In this way, the nut 14 may be threadably advanced along the post 12 toward the outer jaw 22 of the second clamp 34 to exert a clamping force along the axis of the post 12 to the first clamp 32 and the second clamp 16 (as the outer and inner jaws 16, 18 of the first clamp 32 and the inner jaw of the second clamp 34 are positioned between the nut 14 and the outer jaw 22). The threaded post 12 may thereby define the clamping axis X-X of the clamp 10.

As shown in FIGS. 8-12, the clamping device 10 may also include a washer 26 or like mechanism that may extends at least partially about the post 12 and is positioned between the clamping nut 14 and the outer jaw 16 of the first clamp 32. In some embodiments, the washer 26 may be a spherical washer. The washer 26 may include an arcuate or curved inner surface that contacts a corresponding curved outer surface of the outer jaw 16 of the first clamp 32. The engagement of the washer 26 and the corresponding outer surface of the outer jaw 16 of the first clamp 32 may thereby allow angulation of the outer jaw 16 with respect to the post 12 when a clamping force is applied to the clamp 10. For example, the washer 26 may provide a bearing surface on which the outer jaw 16 is able pivot when the backside of the outer jaw 16 and inner jaw 18 engage when a clamping force is applied to the clamp 10 to allow the jaws 16, 18 to transfer some of the clamping forces to the clamping surfaces 30 and, ultimately, to a fixation member positioned therebetween.

The washer 26 or like mechanism may also align the outer jaw 16 with the threaded post 12, and thereby also align at least the inner jaw 18 and the inner jaw 20 with the threaded post 12 and the outer jaw 22 fixed to the post 12 (as they are aligned via engagement with each other). For example, the nut 14 may include an inner projection or lip that engages the washer 26 and aligns the washer 26 in a particular orientation (e.g., normal) to the post 12 (and thereby the clamping axis X-X) when the nut 14 is threadably engaged with the post 12. As explained above, the outer side surface of the washer 26 and the inner side surface of the outer jaw 16 may be arcuate and correspond to each other. For example, the outer side surface of the washer 26 and the inner side surface of the outer jaw 16 may be of a dome shape. The outer jaw 16 may thereby be forced into a particular orientation and positioned with respect to the washer 26 (which is forced into a particular orientation and positioned with respect to the post 12 via the nut 14, as described above). In this way, the outer jaw 16, inner jaw 18 and outer jaw 20 may be aligned with each other and in a particular orientation and positioned with respect to the post 12 (and thereby the clamping axis X-X) when the clamping force is applied. However, when/if the clamping force is greater than the bending strength of stiffness of the components of the clamp, one or more of the components may deform and/or pivot (e.g., angle with respect to the post 12) into a differing orientation or position.

As shown in FIGS. 8-12, the clamping device 10 may also include a resilient member 24 (such as a spring) that maintains the outer and inner jaws 16, 18 of the first clamp 32 in engagement with a fixation member, the outer and inner jaws 20, 22 of the second clamp 34 in engagement with a fixation member, and the first and second clamps 32, 34 in engagement at a particular orientation via a neutral clamping force before a relatively greater fixation clamping force is applied via rotation of the nut 14 (i.e., translation of the nut 14 along the threaded post 12 toward the outer jaw 22). The resilient member 24 may be configured to provide several pounds of neutral or adjustment clamping force, for example, while the nut 14 may be capable of applying tens or hundreds of pounds of fixation clamping force, for example. The resilient member 24 may thereby maintain the relative orientation of the first and second clamps 32, 34, the alignment of the components of the clamp 10, and apply a slight clamping force to the clamping surfaces 30, 28 of the first and second clamps 32, 34. In this way, the clamp 10 can be clamped onto at least one fixation member (e.g., one or more bars or rods and/or pins), and the at least one fixation member (and thereby the clamp 10 as well) can be spatially manipulated or adjusted (e.g., rotated, translated, angled, etc.) while still engaged with the clamp 10. After a desired orientation and position of the at least one fixation member (and thereby the components of the clamp 10 and any fixation components and/or tissue segments coupled to the at least one fixation member) is achieved, the clamping nut 14 can be tightened to exert a relatively high fixation clamping force that locks or fixes the clamp 10 to the at least one fixation member, and thereby fixes the at least one fixation member, the clamp 10 itself (e.g., the relative position of the first and second clamps 32, 34 about the clamping axis X-X, the inner and outer jaws 16, 18 of the first clamp 32, and/or the inner and outer jaws 20, 22 of the second clamp 34, for example), and any other components or tissue segments coupled to the at least one fixation member and the clamp 10 in their desired or corrected orientation and position.

In some embodiments, the resilient member 24 may be positioned between at least a portion of the outer jaw 16 of the first clamp 32 and the clamping nut 14 along the clamping axis X-X. In some embodiments, the resilient member 24 may be positioned to engage the outer jaw 16 of the first clamp 32 and the washer 26 (and/or the clamping nut 14). In some embodiments, the resilient member 24 may be positioned within a cavity or recess within the outer jaw 16 of the first clamp 32, as shown in FIG. 8. The resilient member 24 may exert a force against the outer jaw 16 of the first clamp 32 along the clamping axis X-X toward the outer jaw 22 of the second clamp 34 when the nut 14 is positioned along the post 12 such that the resilient member 24 is elastically deformed. In some embodiments, the clamp 10 may not include (i.e., be void of) another resilient member or spring other the resilient member 24 acting on the outer jaw 16. In some embodiments, the clamp 10 may not include (i.e., be void of) a resilient member or spring that directly acts on the second clamp 34, such as on the inner jaw 20 and/or the outer jaw 22.

Figure 15:
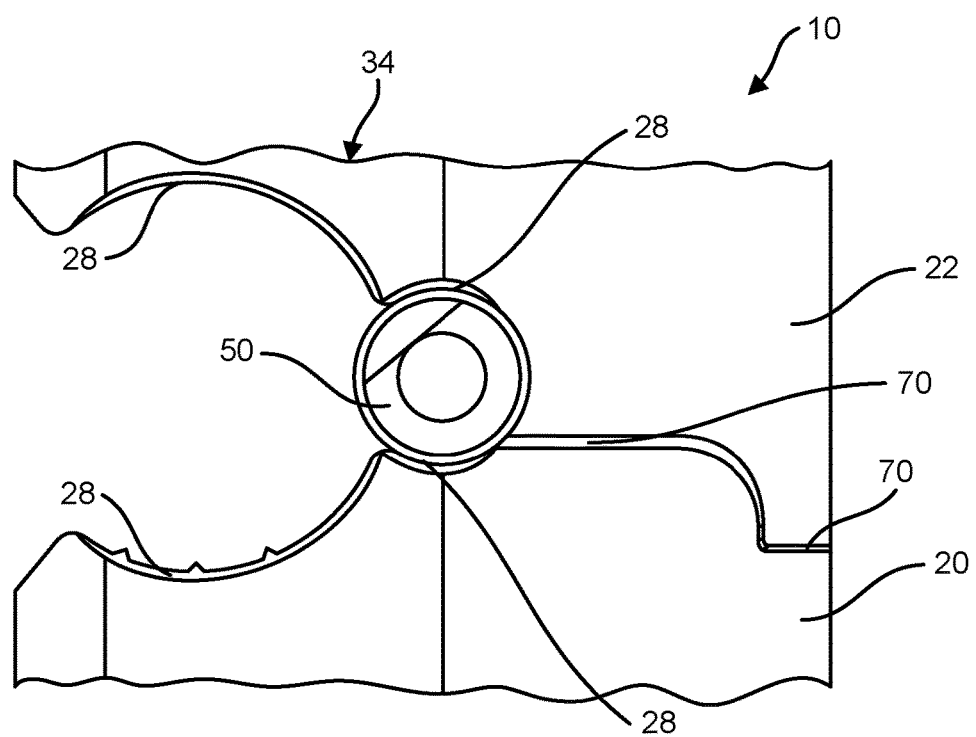
FIG. 15 is a side view of a portion of the orthopedic clamping device of FIG. 1 coupled to the exemplary pin.
Figure 16:
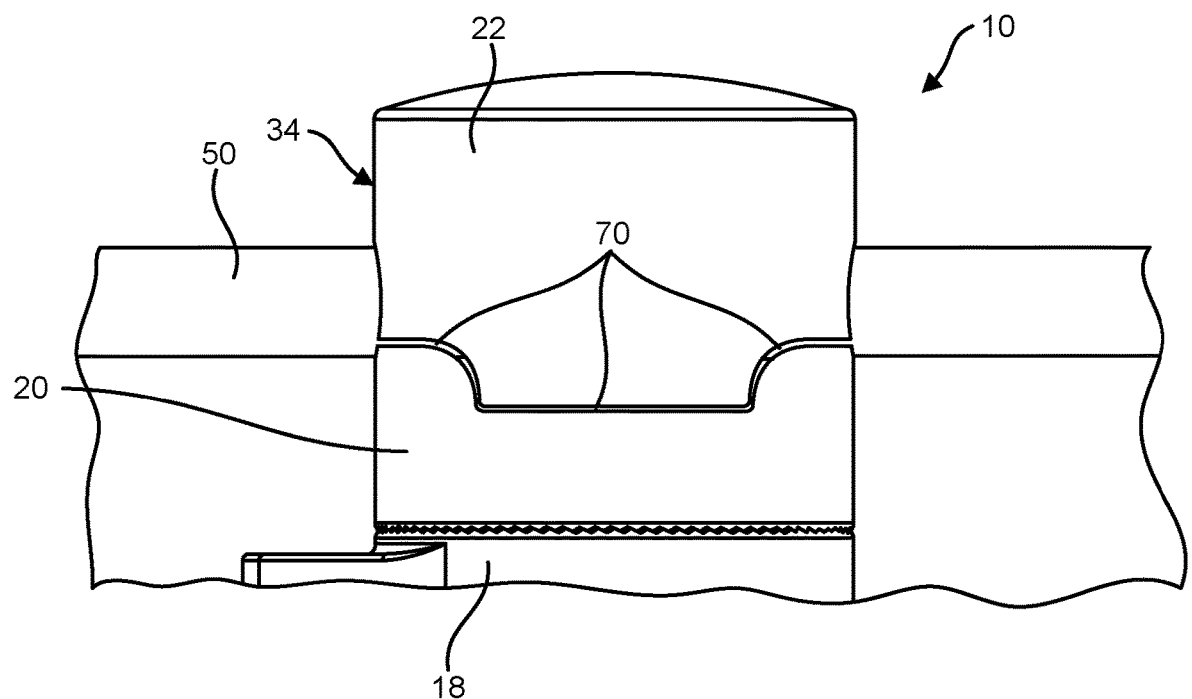
FIG. 16 is a back view of a portion of the orthopedic clamping device of FIG. 1 coupled to the exemplary pin.
Figure 17:
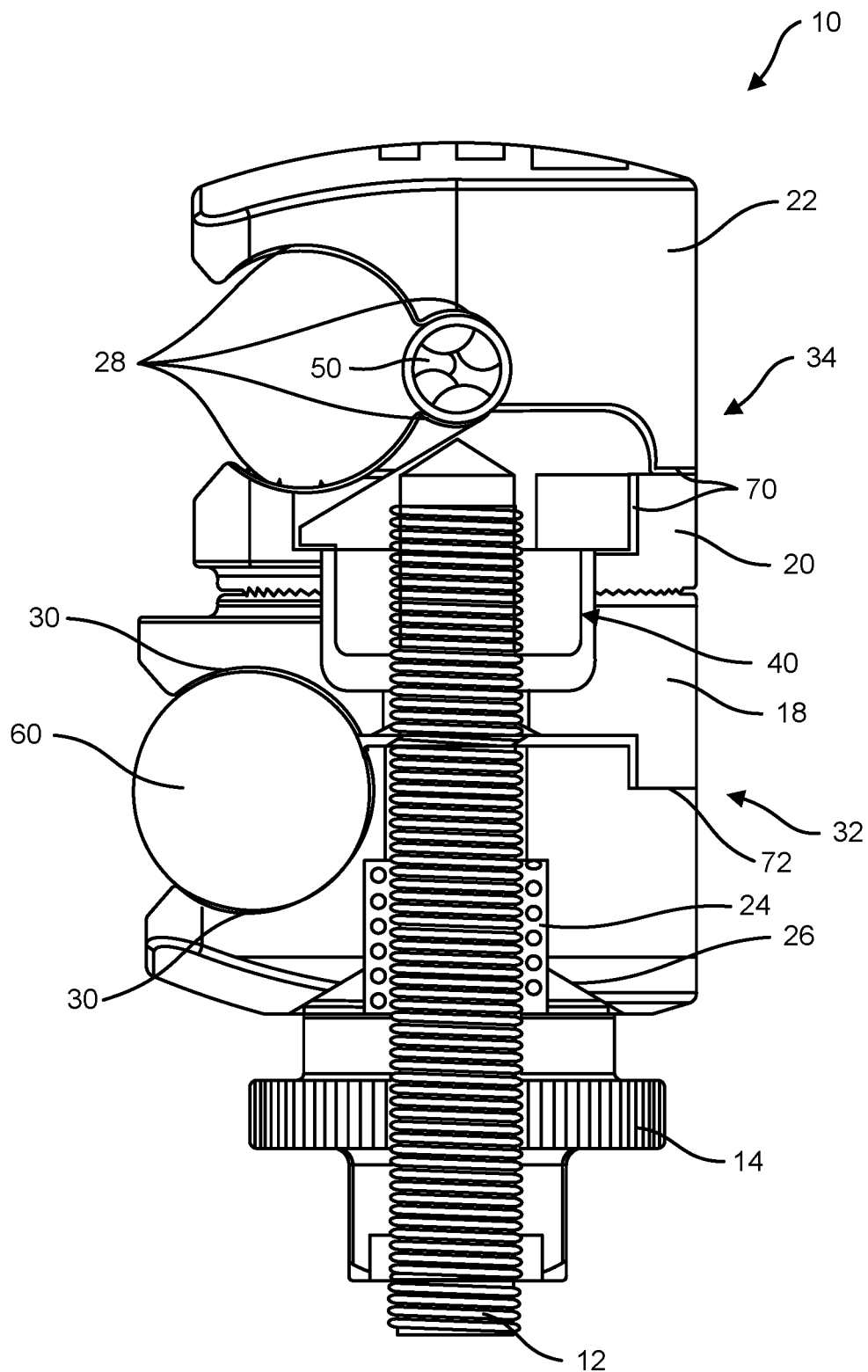
FIG. 17 is a cross-sectional view of the orthopedic clamping device of FIG. 1 coupled to the exemplary pin and the exemplary rod.

As shown in FIGS. 13-17, in some embodiments the clamping device 10 may spatially fix a pin 50 (via the second clamp 34) with a rod or bar 60 (via the first clamp 32) in a desired arrangement. In such an embodiment, the pin 50 may be positioned within the inner cylindrical channel formed by the recessed clamping surface 28 of the inner and outer jaws 20, 22 of the second clamp 34. As explained above, because the axis of the inner cylindrical channel formed by the inner portions of the recessed clamping surface 28 of the inner and outer jaws 20, 22 intersects (and is potentially perpendicular to) the clamping axis X-X (i.e., the compressive force applied to the inner and outer jaws 20, 22 via the clamping nut 14), all (or substantially all) of the clamping force is directed to the pin 50. The adjacent opposing surfaces of the inner and outer jaws 20, 22 thereby are not compressed together (at least to a degree that effectively detracts from the compressive forces on the pin 50) by the clamping force applied to the second clamp 34. For example, as shown in FIGS. 15-17, a gap or space 70 may be present or formed between the inner and outer jaws 20, 22 when a fixation clamping force is applied to the pin 50 by the inner portions of the inner recessed clamping surfaces 28 of the inner and outer jaws 20, 22.

In contrast, as shown in FIG. 17, the inner and outer jaws 18, 16 of the first clamp 32 may abut or contact at a backside 72 of the first clamp 32 when a fixation clamping force is applied to the bar 60 by the recessed clamping surfaces 30 of the inner and outer jaws 18, 16. In this way, the backsides of the inner and outer jaws 18, 16 may abut and cause the inner and outer jaws 18, 16 to pivot such that the recessed clamp surfaces 30 on the front side of the first clamp 32 are moved closer together and/or apply a compressive force to the bar 60, as shown in FIG. 17. The fixation clamping force is thereby split or shared between the backside of the first clamp 32 and the bar 60 (rather than directing all, or substantially all, of the clamping force to the bar 60, as with the inner cylindrical recess of the second clamp 34).

Figure 18:
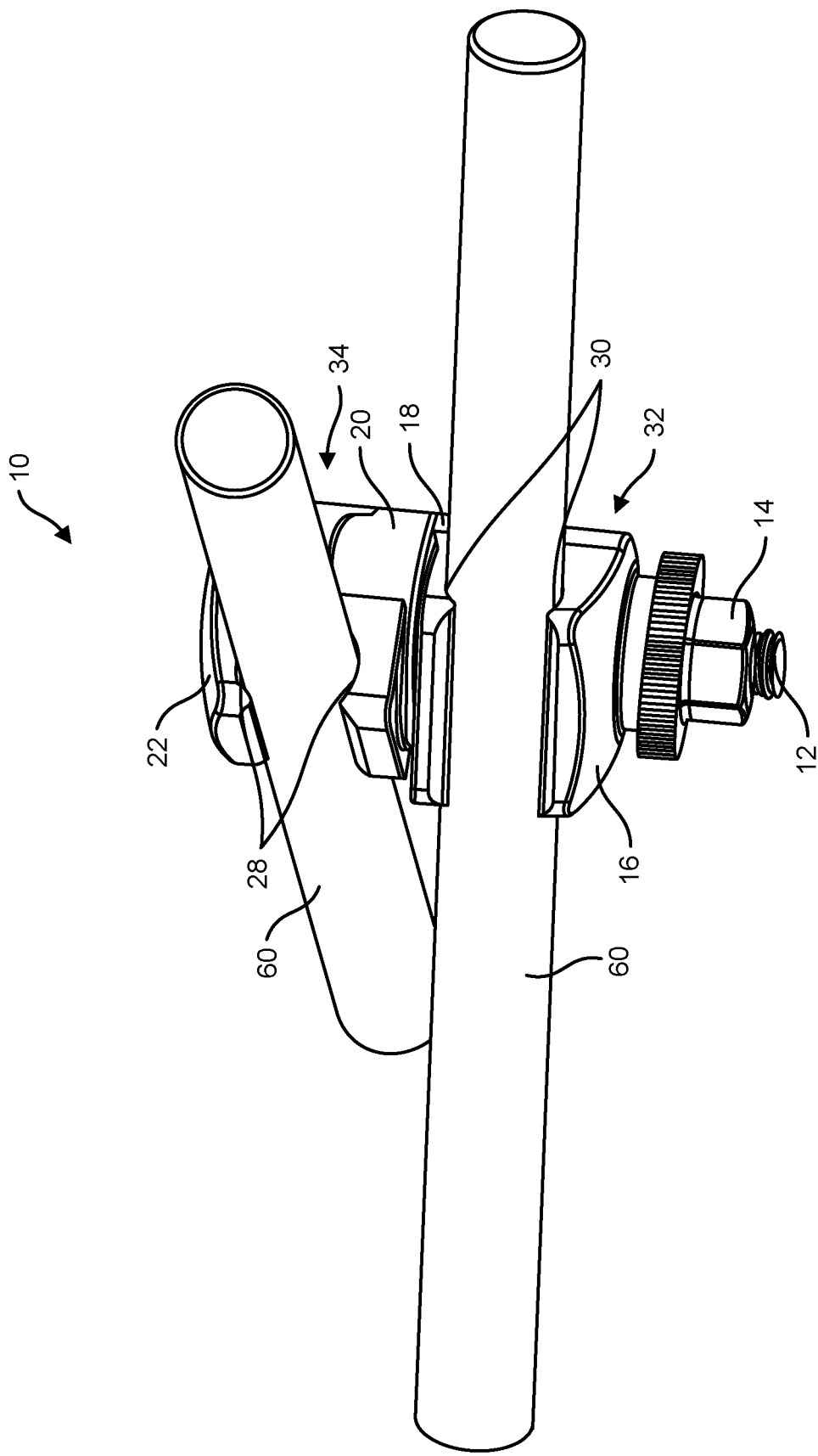
FIG. 18 is a perspective view of the orthopedic clamping device of FIG. 1 coupled to two exemplary rods.
Figure 19:
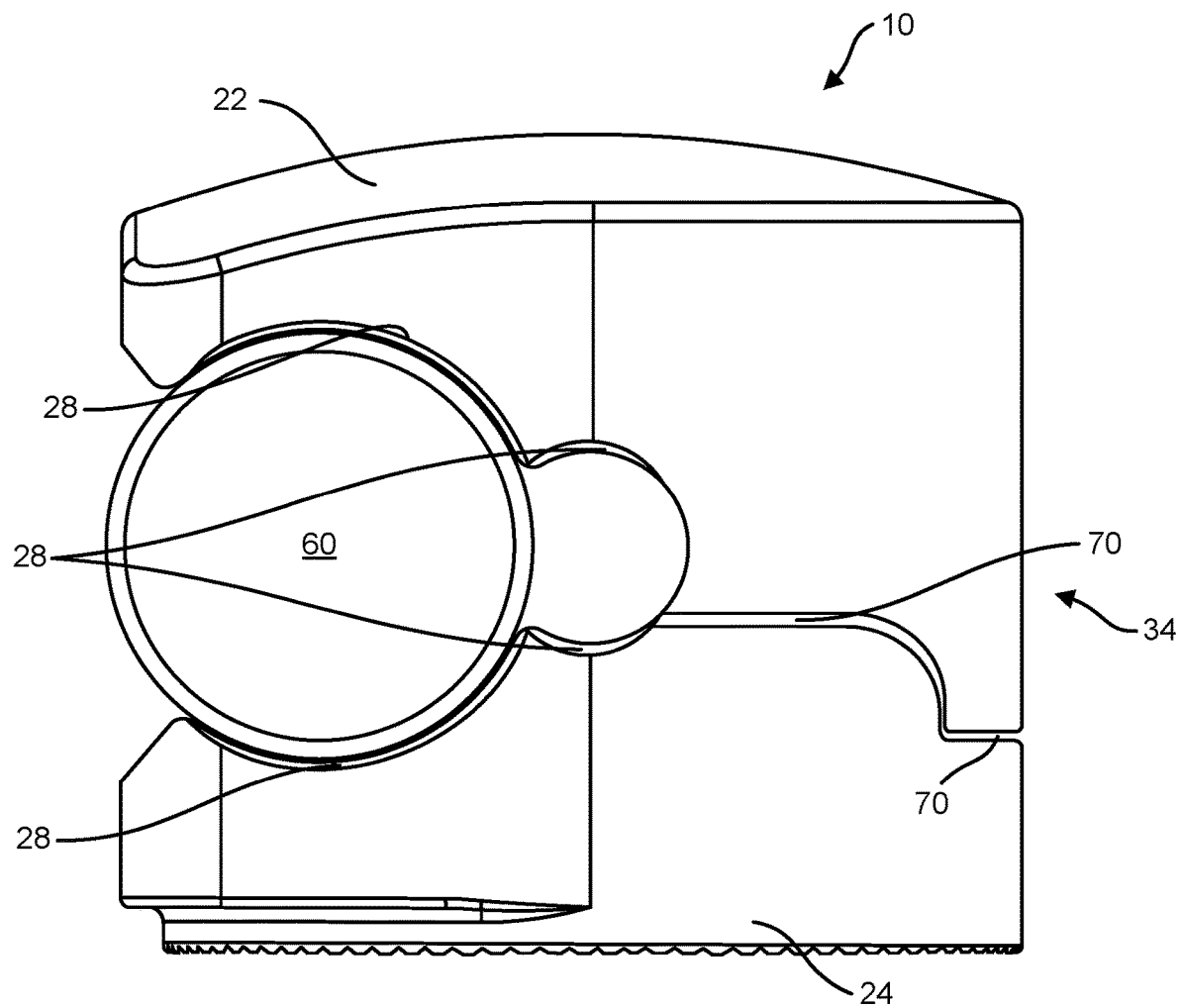
FIG. 19 is a side view of a portion of the orthopedic clamping device of FIG. 1 coupled to the exemplary rod.

As shown in FIGS. 18 and 19, in some embodiments the clamping device 10 may spatially fix a rod or bar 60 via the second clamp 34 in a desired arrangement, such as with another rod or bar 60 via the first clamp 32. In such an embodiment, rod 60 may be positioned within the outer cylindrical channel formed by the outer portions of the recessed clamping surfaces 28 of the inner and outer jaws 20, 22 of the second clamp 34, as shown in FIGS. 18 and 19. Because the axis of the outer cylindrical channel formed by the outer portions of the recessed clamping surface 28 of the inner and outer jaws 20, 22 is offset or spaced from the clamping axis X-X (e.g., the axis thereof does not intersect the clamping axis X-X) (i.e., the compressive force applied to the inner and outer jaws 20, 22 via the clamping nut 14) towards the front side of the second clamp 34, the clamping force will cause the inner and/or outer jaws 20, 22 to pivot such that the backside 72 of the inner and outer jaws 20, 22 are compressed together, as shown in FIG. 19. In this way, the backsides 72 of the inner and outer jaws 20, 22 may abut and compress against each other when the clamping force is applied to the second clamp 34. The fixation clamping force may thereby be split or shared between the backside 72 of the second clamp 34 and the bar 60.

It is to be understood that the above description is intended to be illustrative, and not restrictive. Numerous changes and modifications may be made herein by one of ordinary skill in the art without departing from the general spirit and scope of the disclosure as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A clamp for affixing at least two fixation members relative to each other, comprising:
   a first clamp comprising a first outer jaw and a first inner jaw that define first clamping surfaces that form a first recess that is open to a front side of the first clamp;
   a second clamp comprising a second outer jaw and a second inner jaw that define second clamping surfaces that form second and third recesses that are open to a front side of the second clamp and extend along a width of the second clamp defined by lateral sides thereof;
   a post extending from the second outer jaw and extending through the second inner jaw, the first inner jaw and the first outer jaw, the post defining a clamping axis; and
   a clamping nut threadably coupled to the post configured to exert a clamping force to the first and second clamps to fix at least one of a first fixation member positioned within the first recess and a second fixation member positioned within the second recess,
   wherein the second recess of the second clamp defines an axis that extends along the width of the second clamp and intersects the clamping axis, and
   wherein the post does not extend into the second recess.

2. The clamp of claim 1, wherein the third recess is positioned between the second recess and the front side of the second clamp.

3. The clamp of claim 2, wherein the third recess is open at the front side of the second clamp and the second recess is open to the third recess.

4. The clamp of claim 1, wherein the second fixation member defines an axis, and wherein the axis of the second fixation member intersects the clamping axis when the second fixation member is positioned within the second recess of the second clamp.

5. The clamp of claim 1, wherein the axis of the second recess and the clamping axis are perpendicular.

6. The clamp of claim 1, wherein the first recess of the first clamp defines an axis, and wherein the axis of the first recess is perpendicular to the clamping axis.

7. The clamp of claim 1, further comprising a resilient member that exerts an adjustment clamping force to the first and second clamps to maintain engagement of at least one of the first fixation member within the first recess and the second fixation member within the second recess during manipulation thereof prior to exertion of the fixation clamping force via the clamping nut.

8. The clamp of claim 7, wherein the resilient member is positioned between the first outer jaw and the clamping nut along the clamping axis.

9. The clamp of claim 1, wherein the first inner jaw of the first clamp and the second inner jaw of the second clamp are in abutment along engagement surfaces thereof, and wherein the engagement surfaces of the first and second inner jaws are configured such that the relative rotational arrangement of the first and second clamps about the camping axis is fixed when the clamping force is applied.

10. The clamp of claim 1, wherein the second clamp is configured such that the second outer jaw and the second inner jaw are not compressed together when the clamping force is exerted so that the clamping force is applied to the second fixation member when positioned within the second recess and not directly between the second outer jaw and the second inner jaw.

11. The clamp of claim 1, wherein a first terminal end of the post is positioned within an inner portion of the second outer jaw that is positioned between the second recess and the first clamp.

12. The clamp of claim 1, wherein the second clamping surface of the second outer jaw forms an outer portion of the second recess, and the second clamping surface of the second inner jaw forms an inner portion of the second recess.

13. The clamp of claim 12, wherein the second clamping surface of the second inner jaw comprises a pair of inner surfaces positioned at the lateral sides of the second clamp, and wherein the second inner jaw comprises an internal aperture between the pair of inner surfaces extending axially.

14. The clamp of claim 13, wherein the second outer jaw comprises a stem portion, and wherein at least a portion of the stem portion is positioned within the internal aperture of the second inner jaw.

15. The clamp of claim 1, wherein the second recess is cylindrical.

16. A clamp for affixing at least two fixation members relative to each other, comprising:
- a first clamp comprising a first outer jaw and a first inner jaw that define first clamping surfaces that form a first recess that is open to a front side of the first clamp and is configured to accept a first fixation member therein;
- a second clamp comprising a second outer jaw and a second inner jaw that define second clamping surfaces that form a second recess that is open to a front side of the second clamp and extends along a width of the second clamp defined by lateral sides thereof such that an axis defined by the second recess extends along the width of the second clamp, the second recess configured to accept a second fixation member therein extending along the axis thereof along the width of the second clamp;
- a post extending from the second outer jaw and extending through the second inner jaw, the first inner jaw and the first outer jaw, the post defining a clamping axis that intersects the axis of the second recess; and
- a clamping nut threadably coupled to the post configured to exert a clamping force to the first and second clamps to fix at least one of the first fixation member when positioned within the first recess and the second fixation member when positioned within the second recess,
- wherein the second clamp is configured such that the second outer jaw and the second inner jaw are not compressed together when the clamping force is exerted so that the clamping force is applied to the second fixation member when positioned within the second recess and not directly between the second outer jaw and the second inner jaw.

17. The clamp of claim 16, wherein the second clamp is configured such that the clamping force is not applied to backside surfaces of the of the second outer jaw and the second inner jaw at a back side of the second clamp that is on an opposing side of the clamping axis as the front side of the second clamp when the clamping force is applied to the second fixation member positioned within the second recess.

18. The clamp of claim 17, wherein the second clamp is configured such that a gap is formed between the backside surfaces of the second outer jaw and the second inner jaw when the clamping force is applied to the second fixation member positioned within the second recess.

19. The clamp of claim 16, wherein the axis of the second recess is perpendicular to the clamping axis.

20. A clamp for affixing at least two fixation members relative to each other, comprising:
- a first clamp comprising a first outer jaw and a first inner jaw that define first clamping surfaces that form a first recess that is open to a front side of the first clamp;
- a second clamp comprising a second outer jaw and a second inner jaw that define second clamping surfaces that form a second recess that is open to a front side of the second clamp and extends along a width of the second clamp defined by lateral sides thereof, the second recess defining an axis that extends along the width of the second clamp;
- a post extending from the second outer jaw and past the first outer jaw and defining a clamping axis that intersects the axis of the second recess; and
- a clamping nut threadably coupled to the post configured to exert a clamping force to the first and second clamps to fix at least one of a first fixation member positioned within the first recess and a second fixation member positioned within the second recess, and
- wherein the second recess is void of the post.

21. The clamp of claim 20, wherein the axis of the second recess and the clamping axis are perpendicular.

22. The clamp of claim 20, wherein the second clamp is configured such that the second outer jaw and the second inner jaw are not compressed together when the clamping force is exerted so that the clamping force is applied to the second fixation member when positioned within the second recess and not directly between the second outer jaw and the second inner jaw.

23. The clamp of claim 22, wherein the second clamp is configured such that backside surfaces of the second outer jaw and the second inner jaw at a back side of the second clamp that is on an opposing side of the clamping axis as the front side of the second clamp are not compresses together when the clamping force is applied to the second fixation member positioned within the second recess.

24. The clamp of claim 23, wherein the second clamp is configured such that a gap is formed between the backside surfaces of the second outer jaw and the second inner jaw when the clamping force is applied to the second fixation member positioned within the second recess.

25. The clamp of claim 20, wherein the first inner jaw of the first clamp and the second inner jaw of the second clamp are in abutment along engagement surfaces thereof, and wherein the engagement surfaces of the first and second inner jaws are configured such that the relative rotational arrangement of the first and second clamps about the camping axis is fixed when the clamping force is applied.

26. The clamp of claim 20, further comprising a resilient member that exerts an adjustment clamping force to the first and second clamps to maintain engagement of at least one of the first fixation member within the first recess and the second fixation member within the second recess during manipulation thereof prior to exertion of the fixation clamping force via the clamping nut.

* * * * *